(12) United States Patent
Markowitz et al.

(10) Patent No.: US 7,991,467 B2
(45) Date of Patent: Aug. 2, 2011

(54) REMOTELY ENABLED PACEMAKER AND IMPLANTABLE SUBCUTANEOUS CARDIOVERTER/DEFIBRILLATOR SYSTEM

(75) Inventors: H. Toby Markowitz, Roseville, MN (US); Douglas A. Hettrick, Andover, MN (US); William J. Combs, Minnetonka, MN (US); Todd J. Sheldon, North Oaks, MN (US); David L. Thompson, Andover, MN (US); Raja N. Ghanem, Edina, MN (US); Kevin A. Wanasek, Princeton, MN (US)

(73) Assignee: Medtronic, Inc., Minneapolis, MN (US)

( * ) Notice: Subject to any disclaimer, the term of this patent is extended or adjusted under 35 U.S.C. 154(b) by 75 days.

(21) Appl. No.: 11/114,474

(22) Filed: Apr. 26, 2005

(65) Prior Publication Data

US 2006/0241701 A1 Oct. 26, 2006

(51) Int. Cl.
*A61B 5/02* (2006.01)
*A61N 1/362* (2006.01)
(52) U.S. Cl. .............................. 607/4; 607/14
(58) Field of Classification Search .................. 607/2–5, 607/9, 27, 32, 60, 63, 142, 129, 130
See application file for complete search history.

(56) References Cited

U.S. PATENT DOCUMENTS

| | | | |
|---|---|---|---|
| 3,906,960 A | 9/1975 | Lehr | |
| 3,943,936 A | 3/1976 | Rasor et al. | |
| 4,180,078 A | 12/1979 | Anderson | |
| 4,374,382 A | 2/1983 | Markowitz | |
| 4,485,813 A | 12/1984 | Anderson et al. | |
| 4,556,063 A | 12/1985 | Thompson et al. | |
| 4,693,253 A | 9/1987 | Adams | |
| 4,774,950 A | 10/1988 | Cohen | |
| 4,791,935 A | 12/1988 | Baudino et al. | |
| 4,947,854 A | 8/1990 | Rabinovitz et al. | |
| 4,984,572 A | 1/1991 | Cohen | |
| 4,986,270 A | 1/1991 | Cohen | |
| 4,987,897 A | 1/1991 | Funke | |
| 5,014,698 A | 5/1991 | Cohen | |
| 5,027,816 A | 7/1991 | Cohen | |
| 5,052,388 A | 10/1991 | Sivula et al. | |
| 5,054,485 A | 10/1991 | Cohen | |
| 5,085,213 A | 2/1992 | Cohen | |
| 5,113,859 A * | 5/1992 | Funke .............................. 607/4 |
| 5,119,813 A | 6/1992 | Cohen | |
| 5,127,404 A | 7/1992 | Wyborny et al. | |
| 5,156,148 A | 10/1992 | Cohen | |
| 5,163,429 A | 11/1992 | Cohen | |
| 5,247,945 A * | 9/1993 | Heinze et al. ................. 607/129 |
| 5,269,301 A | 12/1993 | Cohen | |
| 5,271,395 A | 12/1993 | Wahlstrand et al. | |
| 5,330,505 A | 7/1994 | Cohen | |
| 5,354,316 A | 10/1994 | Keimel | |
| 5,360,437 A | 11/1994 | Thompson | |
| 5,368,040 A | 11/1994 | Carney | |
| 5,470,345 A | 11/1995 | Hassler et al. | |
| 5,545,186 A | 8/1996 | Olson et al. | |
| 5,554,177 A | 9/1996 | Kieval et al. | |

(Continued)

*Primary Examiner* — Carl H. Layno
*Assistant Examiner* — Jon-Eric C. Morales
(74) *Attorney, Agent, or Firm* — Michael C. Soblner

(57) ABSTRACT

Subcutaneous Implantable cardioverter-defibrillators (SubQ ICDs) are disclosed that are entirely implantable subcutaneously with minimal surgical intrusion into the body of the patient and provide distributed cardioversion-defibrillation sense and stimulation electrodes for delivery of cardioversion-defibrillation shock and pacing therapies across the heart when necessary. The SubQ ICD is implemented with other implantable and external medical devices and communicates to provide drugs and therapy in a coordinated and synergistic manner.

8 Claims, 8 Drawing Sheets

U.S. PATENT DOCUMENTS

| | | |
|---|---|---|
| 5,662,689 A | 9/1997 | Elsberry et al. |
| 5,683,432 A | 11/1997 | Goedeke et al. |
| 5,814,089 A | 9/1998 | Stokes et al. |
| 5,817,131 A | 10/1998 | Elsberry et al. |
| 5,855,593 A | 1/1999 | Olson et al. |
| 5,893,881 A | 4/1999 | Elsberry et al. |
| 6,141,588 A | 10/2000 | Cox et al. |
| 6,266,567 B1* | 7/2001 | Ishikawa et al. ............... 607/36 |
| 6,280,461 B1 | 8/2001 | Glegyak et al. |
| 6,453,195 B1* | 9/2002 | Thompson ........................ 607/3 |
| 6,470,212 B1 | 10/2002 | Weijand et al. |
| 6,497,655 B1 | 12/2002 | Linberg et al. |
| 6,512,949 B1 | 1/2003 | Combs et al. |
| 6,690,959 B2 | 2/2004 | Thompson |
| 7,260,433 B1* | 8/2007 | Falkenberg et al. ............ 607/14 |
| 2002/0133196 A1* | 9/2002 | Thompson ........................ 607/3 |
| 2003/0158584 A1 | 8/2003 | Cates et al. |
| 2004/0077995 A1* | 4/2004 | Ferek-Petric et al. .......... 604/66 |
| 2004/0133242 A1* | 7/2004 | Chapman et al. ................ 607/5 |
| 2004/0158294 A1 | 8/2004 | Thompson |
| 2004/0215239 A1* | 10/2004 | Favet et al. ....................... 607/4 |
| 2004/0220628 A1 | 11/2004 | Wagner |
| 2005/0049656 A1 | 3/2005 | Petersen et al. |
| 2005/0055056 A1* | 3/2005 | Olson ................................ 607/5 |
| 2005/0076909 A1* | 4/2005 | Stahmann et al. ....... 128/204.23 |
| 2006/0173498 A1* | 8/2006 | Banville et al. ................... 607/5 |

* cited by examiner

REMOTELY ENABLED PACEMAKER AND IMPLANTABLE SUBCUTANEOUS CARDIOVERTER/DEFIBRILLATOR SYSTEM

FIELD OF THE INVENTION

The present invention generally relates to an implantable medical device system, particularly comprising a subcutaneous implantable cardioverter-defibrillator (SubQ ICD) that is entirely implanted subcutaneously with no endovascular or epicardial leads/electrodes. More specifically, the SubQ ICD is in bi-directional data communication and functional synergy with one or more implantable and/or externally mounted devices and, optionally to a transdermal drug delivery apparatus.

BACKGROUND OF THE INVENTION

Many types of implantable medical devices (IMDs) have been clinically implanted over the last twenty years that deliver relatively high-energy cardioversion and/or defibrillation shocks to a patient's heart when a malignant tachyarrhythmia, e.g., atrial or ventricular fibrillation, is detected. Cardioversion shocks are typically delivered in synchrony with a detected R-wave when fibrillation detection criteria are met, whereas defibrillation shocks are typically delivered when fibrillation criteria are met and an R-wave cannot be discerned from the electrogram (EGM).

The current state of the art of ICDs or implantable pacemaker/cardioverter/defibrillators (PCDs) includes a full featured set of extensive programmable parameters which includes multiple arrhythmia detection criteria, multiple therapy prescriptions (for example, stimulation for pacing in the atrial, ventricular and dual chamber; atrial and ventricular for bradycardia; bi-atrial and/or bi-ventricular for heart failure; and arrhythmia overdrive or entrainment stimulation; and high level stimulation for cardioversion and/or defibrillation), extensive diagnostic capabilities and high speed telemetry systems. These full-featured ICDs or PCDs, hereinafter IMD, are typically implanted into patients who have had, and survived, a significant cardiac event such as sudden death. Additionally, these devices are expected to last up to 5-8 years and/or provide at least 200 life saving therapy shocks.

Even though there have been great strides in size reduction over the past 20 years, the incorporation of all these features in an IMD, including the longevity requirements, dictates that the devices be typically much larger than current state of the art pacemakers. Such devices are often difficult to implant in some patients (particularly children and thin, elderly patients) and typically require the sacrifice of 1 or 2 veins to implant the lead system because leads associated with implantation of an IMD utilize a transvenous approach for cardiac electrodes and lead wires. The defibrillator canister/housing is generally implanted as an active can for defibrillation and electrodes positioned in the heart are used for pacing, sensing and detection of arrhythmias.

Although IMDs and implant procedures are very expensive, most patients who are implanted have experienced and survived a sudden cardiac death episode because of interventional therapies delivered by the IMDs. Survivors of sudden cardiac death episodes are in the minority, and studies are ongoing to identify patients who are asymptomatic by conventional measures but are nevertheless at risk of a future sudden death episode. Current studies of patient populations, e.g., the MADIT II and SCDHeFT studies, are establishing that there are large numbers of patients in any given population that are susceptible to sudden cardiac death, that they can be identified with some degree of certainty and that they are candidates for a prophylactic implantation of a defibrillator (often called primary prevention). However, implanting currently available IMDs in all such patients would be prohibitively expensive. Further, even if the cost factor is eliminated there is shortage of trained personnel and implanting resources.

One option proposed for this patient population is to implant a prophylactic subcutaneous implantable cardioverter/defibrillator (SubQ ICD) such that when these patients receive a shock and survive a cardiac episode, they will ultimately have an implant with a full-featured ICD and transvenous leads.

While there are a few small populations in whom SubQ ICD might be the first choice of implantation for a defibrillator, the vast majority of patients are physically suited to be implanted with either an ICD or SubQ ICD. It is likely that pricing of the SubQ ICD will be at a lower price point than an ICD. Further, as SubQ ICD technology evolves, it may develop a clear and distinct advantage over ICDs. For example, the SubQ ICD does not require leads to be placed in the bloodstream. Accordingly, complications arising from leads placed in the cardiovasculature environment is eliminated. Further, endocardial lead placement is not possible with patients who have a mechanical heart valve implant and is not generally recommended for pediatric cardiac patients. For these and other reasons, a SubQ ICD may be preferred over an ICD.

There are technical challenges associated with the implantation of a SubQ ICD. For example, SubQ ICD sensing is challenged by the presence of muscle artifact, respiration and other physiological signal sources. This is particularly because the SubQ ICD is limited to far-field sensing since there are no endocardial or epicardial electrodes in a subcutaneous system. Further, sensing of atrial activation from subcutaneous electrodes is limited since the atria represent a small muscle mass and the atrial signals are not sufficiently detectable transthoracically. Thus, SubQ ICD sensing presents a bigger challenge than an ICD which has the advantage of electrodes in contact with the heart and, especially, inside the atrium. Accordingly, the design of a SubQ ICD is a difficult proposition given the technical challenges to sense and detect arrhythmias.

Yet another challenge could be combining a SubQ ICD with an existing pacemaker (IPG) in a patient. While this may be desirable in a case where an IPG patient may need a defibrillator, a combination implant of SubQ ICD and IPG may result in inappropriate therapy pace or shock by the SubQ ICD, due to inappropriate sensing of spikes from the IPG. Specifically, each time the IPG emits a pacing stimulus, the SubQ ICD may interpret it as a genuine cardiac beat. The result can be over-counting beats from the atrium, ventricles or both; or, because of the larger pacing spikes, sensing of arrhythmic signals (which are typically much smaller in amplitude) may be compromised.

Further, there may be patients who first receive a SubQ ICD and then develop bradycardia. This may occur with the use of beta-blockers, medical management of atrio-ventricular conduction due to development of atrial fibrillation or sinus node disease. Once patients have a SubQ ICD, it makes sense not to abandon the SubQ ICD system but leverage the SubQ ICD with a compatible IPG. Similarly, there may be an interest in patients who receive a SubQ ICD and then have an inappropriate shock. These patients may need an upgrade to an ICD, but they, too, could benefit from the use of a SubQ ICD compatible IPG.

Additionally, the implanting of two or more devices in a patient can be challenging with respect to programming and coordinating therapies delivered by the devices. Further, monitoring of the patient including the devices by use of conventional telemetry and diagnostics may pose additional burden on patient and device management resources. Additionally, several scenarios may arise in which an external defibrillator may be used on patients with an implantable SubQ ICD, a pacemaker, or both. A typical example is an emergency situation in which a patient with an IPG has collapsed and a rescue procedure is conducted. In this scenario, it is likely that an automatic external defibrillator (AED) may be used on the patient. It is therefore important that the IPG and the AED establish communications to coordinate therapy delivery activities. This includes arrhythmia detection, direction to charge/discharge each defibrillator, the delivery of a shock(s) and device protection. Specifically, the operations of one device may be suspended when one another device is providing a life support therapy.

Similarly, a SubQ ICD and an AED may cooperate to provide needed therapy. For example, if the SubQ ICD is not capable of restoring sinus rhythm, the AED may be given a chance to do it unaffected by the SubQ ICD. However, if the SubQ ICD is incapable of supplying sufficient energy, the combination of the SubQ ICD and the AED might be useful. In this setting, the SubQ ICD and AED could collaborate such that they shock simultaneously. The polarity must be coordinated such that the fields are additive or, alternatively, the concept of rotating fields may be Implemented. The AED patches could be positioned such that the first shock is delivered by one device and, after a further short delay, the second shock is delivered by one device and, after a short delay, the third shock is delivered with a slightly different orientation. This latter concept is well known in the art. With a SubQ ICD and an AED having two entirely separate sets of electrodes, it is feasible that the two could collaborate in this manner if they have inter-device communications. So it is envisioned that an AED could be in place in addition to a pacemaker and/or SubQ ICD. This could be a hospital setting such as a CCU or an ER. It could also be advanced life support as part of the emergency medical system with EMTs or paramedics.

Additionally, during cardioversion/defibrillation therapy delivery by either the AED or SubQ ICD, the IMD can take precautions to prevent damage due to high current flow and high voltage spikes.

Therefore, for these and other reasons, a need exists for a bi-directional communication system between an IPG and SubQ ICD, or alternatively, between an AED and an IPG and/or SubQ ICD. The IPG, by virtue of it having leads within the heart, should greatly improve the specificity of arrhythmia detection and allow additional therapy options, such as automatic tachycardia pacing (ATP). The IPG and SubQ ICD should be able to communicate wirelessly, either through RF or other intra-body communications medium.

When either device, the IPG or SubQ ICD detects the presence of another device it would go into a cooperative mode and operates accordingly. The IPG and the SubQ ICD, for example, should cooperate in such a way that the IPG would handle tachycardia detection and be in charge of directing charging and delivery of shocks. When the IPG detects a potentially shockable rhythm, it can direct the SubQ ICD to charge and then deliver a shock. If the rhythm might be pace terminable, the IPG can attempt ATP. During this time, it can direct the SubQ ICD to charge the capacitors and enters a stand by mode. Upon failure to convert the cardiac rhythm, the IPG would then direct the SubQ ICD to deliver a shock.

Conversely, the IPG should be in continuous communications with the SubQ ICD and anticipates the possibility that the SubQ ICD may issue a shock. At the time the SubQ ICD issues a shock, the IPG should protect itself and prepare for post-shock sensing and detection. If the IPG is unsure as to whether the rhythm is one requiring a shock, the IPG and SubQ ICD can perform a crosscheck to improve the confidence of arrhythmia detection.

Utilization of a SubQ ICD and IPG, may avoid the risk and morbidity associated with removal of an IPG to upgrade to an ICD, for example. In this case pacing leads may need to be removed or left in the vasculature while additional defibrillation leads should be implanted, thus crowding the veins. Alternatively, a SubQ ICD may be subcutaneously implanted and the IPG upgraded to communicate with the SubQ ICD. Thus, the need to replace the intracardiac pacing leads and the attendant risks could be eliminated.

SUMMARY OF THE INVENTION

The present invention provides a method and apparatus that provides a bi-directional communication system to allow external (AED), subcutaneous (SubQ ICD) and implantable medical devices (IMD) such as an IPG to communicate in order to coordinate the delivery of therapy.

In one embodiment, a continuous communication and automatic initialization of an IMD and SubQ ICD is implemented to perform synergistic detection of arrhythmic episodes and deliver a coordinated effective therapy as needed.

A still further embodiment relates to a communication system between a pain-suppressing device such that a bolus of pain suppression drug is released into the patient to reduce pain and discomfort associated with high voltage stimulation.

In yet another embodiment, a control system and computer-implemented software coordinate monitoring and communications between one or more external, subcutaneous and implanted devices. Specifically, controls and screen displays are implemented to enable safe and effective operations.

BRIEF DESCRIPTION OF THE DRAWINGS

These and other features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE INVENTION

Figure 1:
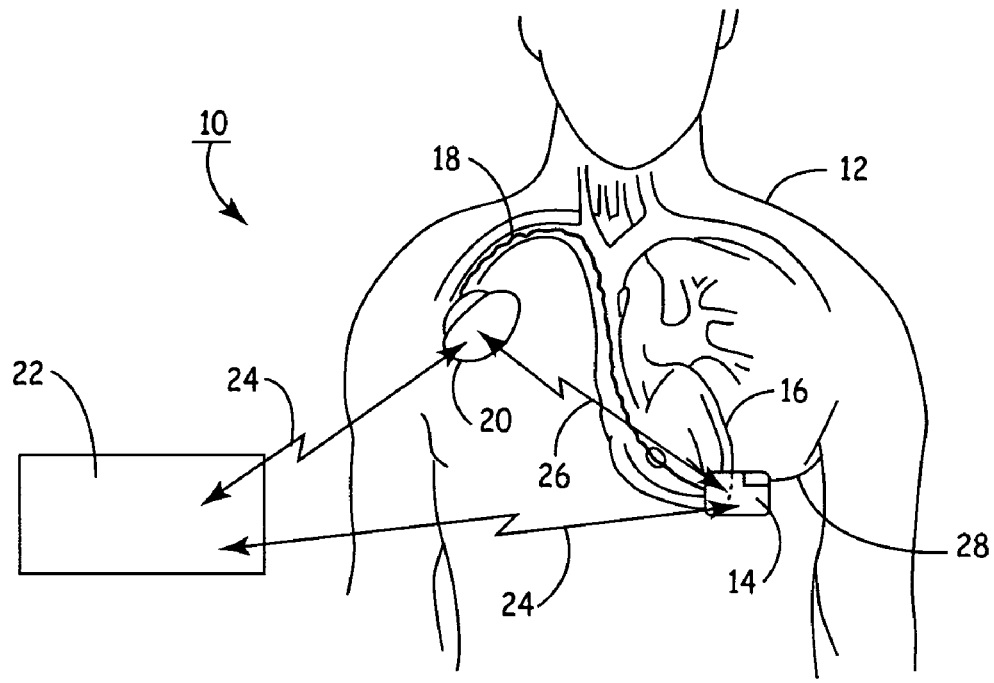
FIG. 1 illustrates a SubQ ICD and IMD of a first embodiment with the devices implanted in a patient.

FIG. 1 illustrates a first embodiment of the present invention, having a SubQ ICD 14 and IMD 20 implanted in patient 12. The SubQ ICD 14 is subcutaneously implanted outside the ribcage of patient 12 anterior to the cardiac notch. SubQ ICD 14 is shown coupled to subcutaneous lead 28. Lead 28 includes an electrode for subcutaneous sensing and cardioversion/defibrillation therapy delivery and is located transthoracically in relation to heart 16. Lead 28 is tunneled subcutaneously from the median implant pocket of SubQ ICD 14 laterally and posteriorly to the patient's back to a location opposite the heart such that the heart 16 is disposed between the SubQ ICD 14 and the distal electrode coil 29 (see FIG. 3). The implant location of device 14 and lead 28 is typically between the $3^{rd}$ and $8^{th}$ ribs.

IMD 20 is shown implanted pectorially in patient 12 and may take the form of any type of pacemaker/stimulator such as, but not limited to, a single chamber atrial pacemaker, a single chamber ventricular pacemaker, a dual chamber atrial/ventricular pacemaker, a bi-atrial pacemaker, a bi-ventricular pacemaker and the like. Cardiac lead(s) 18 are shown implanted in the right ventricle of heart 16. However, cardiac lead(s) 18 may take the form of any typical lead configuration as is known in the art, such as, without limitation, right ventricular (RV) pacing or defibrillation leads, right atrial (RA) pacing or defibrillation leads, single pass RA/RV pacing or defibrillation leads, coronary sinus (CS) pacing or defibrillation leads, left ventricular pacing or defibrillation leads, pacing or defibrillation epicardial leads, subcutaneous defibrillation leads, unipolar or bipolar lead configurations, or any combinations of the above lead systems.

Further referring to FIG. 1, programmer 22 is shown in telemetric communication with IMD 20 and SubQ ICD 14 by RF communication 24 such as Bluetooth, WiFi, MICS, or as described in U.S. Pat. No. 5,683,432 "Adaptive Performance-Optimizing Communication System for Communicating with an Implantable Medical Device" to Goedeke, et al and incorporated herein by reference in its entirety. A bi-directional wireless link 26 is shown allowing communication between IMD 20 and SubQ ICD 14. The wireless communication link 26 may consist of an RF link such as Bluetooth, WiFi, MICS, or as described in the above referenced '432 patent to Goedeke. Further, the wireless communication line 26 may consist of an electromagnetic/ionic transmission such as described in U.S. Pat. No. 4,987,897 "Body Bus Medical Device Communication System" to Funke and incorporated herein by reference in its entirety or acoustic transmission such as described in U.S. Pat. No. 5,113,859 "Acoustic Body Bus Medical Device Communication System" to Funke and incorporated herein by reference in its entirety.

The functional and operational protocol set of IMD 20 may also be upgraded by downloadable software updates using programmer 22 when SubQ ICD 14 is implanted to cooperatively support additional therapy. For example, a simple pacemaker may be updated to include arrhythmia detection algorithms, ATP stimulation therapy capabilities, arrhythmia diagnostic capabilities, system details to allow the control of SubQ ICD 14 and the like. The code may be downloaded using the method described in U.S. Pat. No. 5,360,437 "Implantable Medical Device with Flexible Hardware Platform" to Thompson incorporated herein by reference in its entirety.

Figure 2:
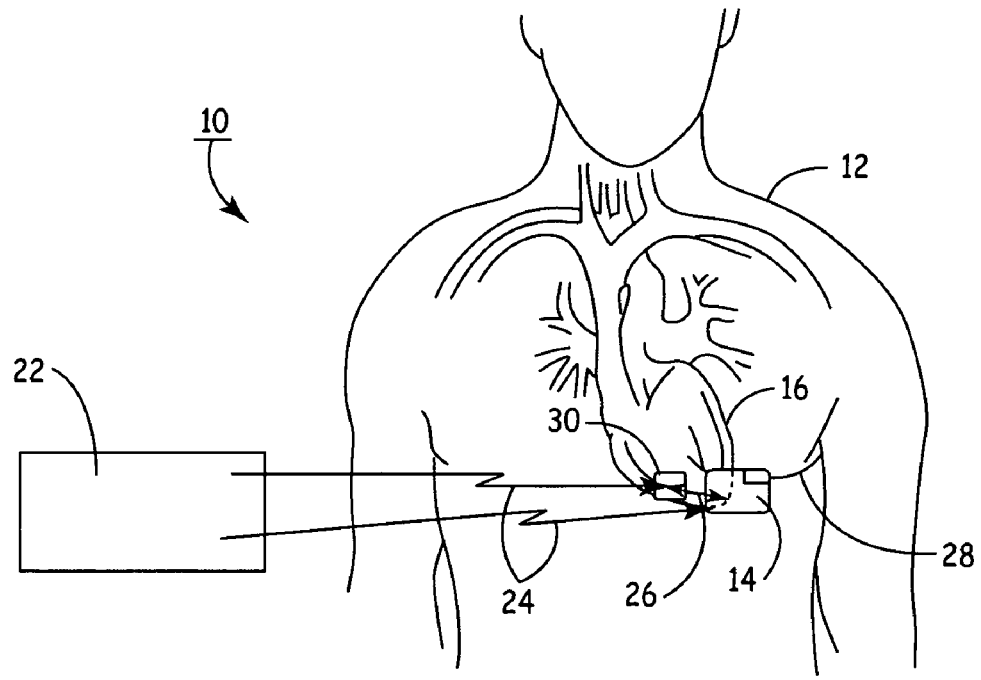
FIG. 2 illustrates a SubQ ICD and IMD of a second embodiment with the devices implanted in a patient.

FIG. 2 illustrates a second embodiment of the present invention having SubQ ICD 14 and IMD 30 implanted in patient 12. The SubQ ICD 14 is subcutaneously implanted outside a patient's 12 ribcage similar to the description hereinabove.

IMD 30 is shown implanted epicardially in patient 12 and may take the form of any type of pacemaker/stimulator such as, but not limited to, a single chamber atrial pacemaker, a single chamber ventricular pacemaker, a dual chamber atrial/ventricular pacemaker, a bi-atrial pacemaker, a bi-ventricular pacemaker and the like. Cardiac leads/electrodes (not shown in FIG. 2) connect IMD 30 to the patient's heart 16 and may take the form of any typical lead configuration as is known in the art, such as, without limitation, epicardial right ventricular (RV) pacing leads, right atrial (RA) pacing leads, left ventricular pacing leads, unipolar or bipolar lead/electrode configurations, or any combinations of the above lead systems. Epicardial lead/electrode attachment to the heart may consist of hooks, barbs or screw-in electrodes. Alternatively, nano-teeth or electrodes may be used such as described in U.S. Pat. No. 6,690,959 "Skin-Mounted Electrodes with Nano Spikes" to Thompson and incorporated herein by reference in its entirety.

The epicardial IMD 30 may optionally provide cardiac mechanical motion, strain, and dynamic pressure measurements. Specifically, device mounted sensors utilizing the piezoelectric effect of semiconductor material making up the nanoteeth or electrodes may be used for these measurements as described above in relation to the Thompson '959 patent.

Continuing with FIG. 2, programmer 22 is shown in telemetric communication with IMD 30 and SubQ ICD 14 by RF communication 24 such as described in the above referenced '432 patent to Goedeke. A bi-directional wireless link 26 is shown enabling communication between IMD 30 and SubQ ICD 14. The wireless communication link 26 may consist of an RF link such as Bluetooth, WiFi, MICS, or as described in the above referenced '432 patent to Goedeke, an electromagnetic/ionic transmission such as described in the above referenced '897 patent to Funke or acoustic transmission such as described in the above referenced '859 patent to Funke.

IMD 30 does not deliver therapy and therefore no stimulus energy will be required. Accordingly, the epicardial IMD 30 of FIG. 2 may optionally consist only of a sensing function and be rechargeable or self-powered. An accelerometer power source such as described in U.S. Patent Application No. 2004/0158294 to Thompson may be used to generate adequate power to provide sensing of cardiac arrhythmias and limited telemetry function to notify/communicate with SubQ ICD 14 via channel 26. Alternatively, RF may be used to periodically recharge the battery to provide the same limited sensing and communication function. A second alternative power source may consist of a small magnet moveable in a small coil to generate a voltage to again provide power and enable limited sensing and communication function.

Figure 3:
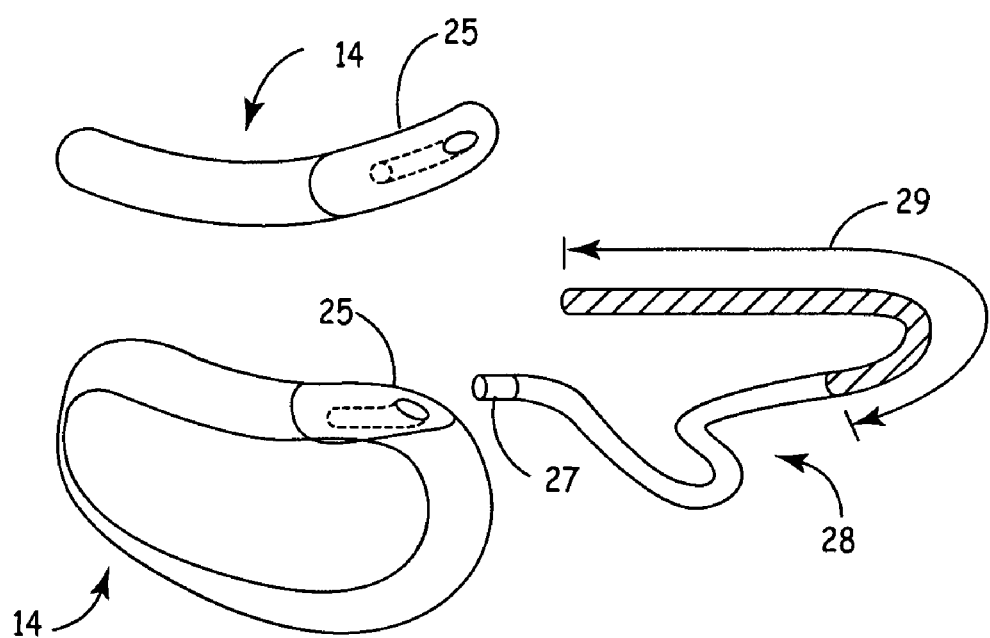
FIG. 3 illustrates a front elevation and a SubQ ICD with the associated subcutaneous lead and electrode.

FIG. 3 illustrates a front elevation and plan view of a SubQ ICD 14 and lead 28 of the present invention. SubQ ICD 14 includes a convex, kidney-shaped ovoid housing with connector block 25 for attaching a subcutaneous sensing and cardioversion/defibrillation therapy delivery lead 28. SubQ ICD 14 may be constructed of stainless steel, titanium or ceramic as described in U.S. Pat. No. 4,180,078 "Lead Connector for a Body Implantable Stimulator" to Anderson and U.S. Pat. No. 5,470,345 "Implantable Medical Device with Multi-layered Ceramic Enclosure" to Hassler, et al. The electronics circuitry of subcutaneous cardioverter-defibrillator 14, as described hereinbelow, may be incorporated on a polyamide flex circuit, printed circuit board (PCB) or ceramic substrate with integrated circuits packaged in leadless chip carriers and/or chip scale packaging (CSP). The convex curvature in combination with the substantially flat bottom of SubQ ICD 14 enables unobtrusive subcutaneous implant. Specifically, the curvature enables deployment tracking the natural curve of the patient's median ribcage at the cardiac notch. This structure also minimizes patient discomfort particularly because of the upper arcuate depression on the housing that accommodates compressive forces and allows for muscle and movement of the ribs thus reducing patient discomfort when seated, bending over and/or during normal torso movement.

Figure 4A:
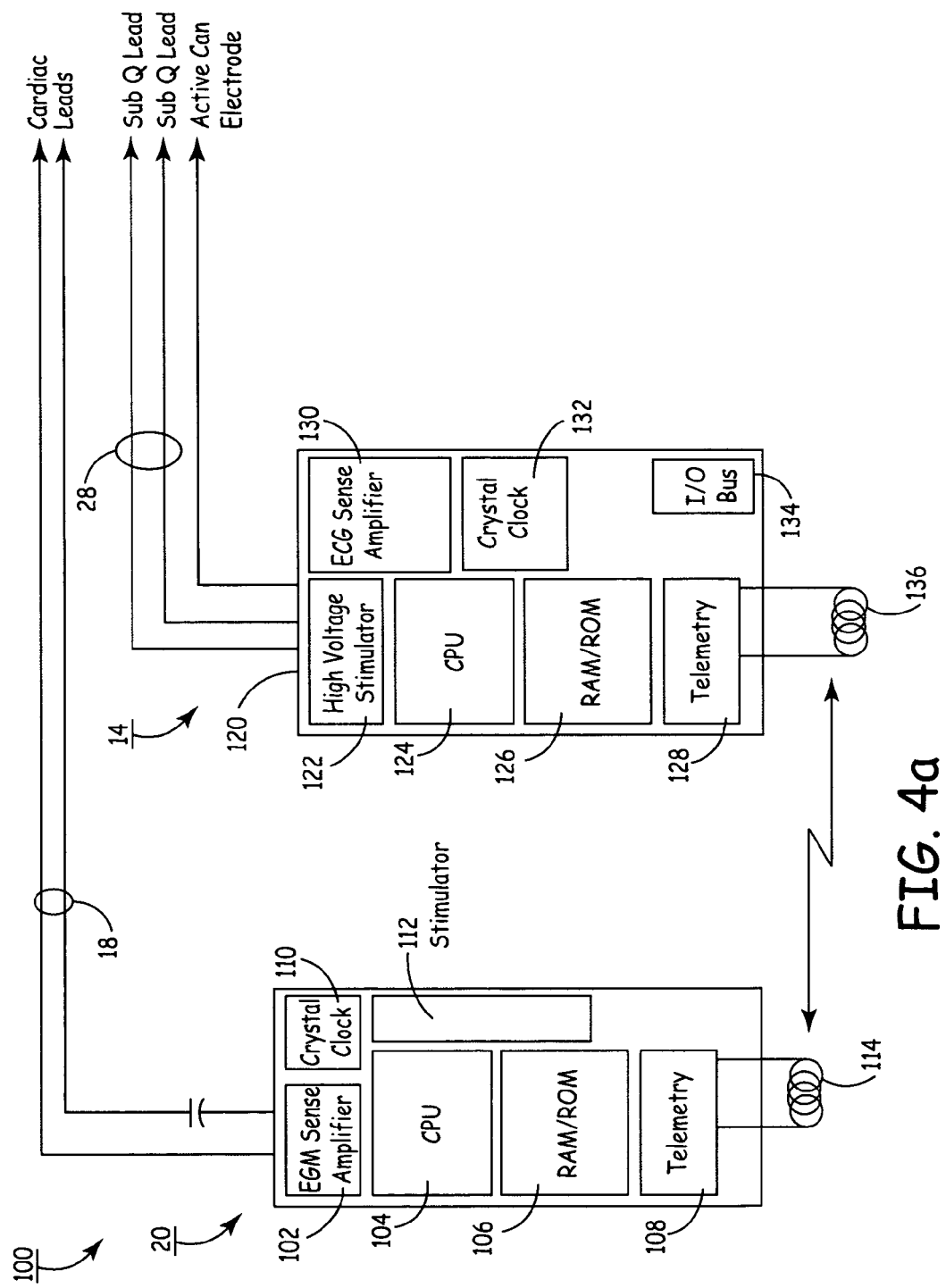
FIG. 4A illustrates the circuitry of the SubQ ICD and IMD.

FIG. 4a illustrates the electronic circuitry for SubQ ICD 14 and IMD 20 in accordance with the present invention. To the extent that certain components of SubQ ICD 14 and IMD 20 are conventional in their design and operation, such components will not be described herein in detail, as it is believed that design and implementation of such components would be well known to those of ordinary skill in the art. As illustrated in FIG. 4A, SubQ ICD 14 comprises a primary control circuit 120. Much of the circuitry associated with primary control circuit 120 is of conventional design, in accordance, for example, with what is disclosed in U.S. Pat. No. 5,354,316 "Method and Apparatus for Detection and Treatment of Tachycardia and Fibrillation" to Keimel; 5,545,186 "Prioritized Rule Based Method and Apparatus for Diagnosis and Treatment of Arrhythmias" to Olson, et al and U.S. Pat. No. 5,855,593 "Prioritized Rule Based Method and Apparatus for Diagnosis and Treatment of Arrhythmias" to Olson, et al (all incorporated herein by reference in their entireties). Primary control circuit 120 includes ECG sense amplifier circuitry 130 for sensing cardiac activity from subcutaneous lead(s) and a housing 14 electrode, a crystal clock 132, a random-access memory and read-only memory (RAM/ROM) unit 126, a central processing unit (CPU) 124 and a telemetry circuit 128, all of which are well known in the art. It is to be understood that the various components of SubQ ICD 14 are powered by means of a battery (not shown), which is contained within the hermetic enclosure of SubQ ICD 14, in accordance with common practice in the art. The battery can comprise one or two conventional LiSVO or LiMnO$_2$ cells. For the sake of clarity in the figures, the battery and the connections between it and the other components of SubQ ICD 14 are not shown.

SubQ ICD 14 desirably includes telemetry circuit 128, in conjunction with antenna 136, so that it is capable of being programmed by means of external programmer 22 via a 2-way telemetry link 24 (shown in FIGS. 1 and 2). Uplink telemetry allows device status and diagnostic/event data to be sent to external programmer 22 for review by the patient's physician. Programmers and telemetry systems suitable for use in the practice of the present invention have been well known for many years. Known programmers typically communicate with an implanted device via a bi-directional radio-frequency telemetry link, so that the programmer can transmit control commands and operational parameter values to be received by the implanted device, and also the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn. Various telemetry systems for providing the necessary communications channels between an external programming unit and an implanted device have been developed and are well known in the art. Telemetry systems believed to be suitable for the purposes of practicing the present invention are disclosed, for example, in the following U.S. Patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties.

A two-way wireless telemetry communication link 26 connects the IMD 20 and SubQ ICD 14 via antennas 114 and 136 and telemetry blocks 108 and 128, respectively. The wireless communication link 26 may consist of an RF link such as Bluetooth, WiFi, MICS, or as described in the above referenced '432 patent to Goedeke and incorporated herein by reference in its entirety, an electromagnetic/ionic transmission such as described in the above referenced '897 patent to Funke and incorporated herein by reference in its entirety or acoustic transmission such as described in the above referenced '859 patent to Funke and incorporated herein by reference in its entirety. IMD 20 additionally contains an amplifier 102 to amplify and sense EGM signals from cardiac implanted lead(s) 18, an output stimulator 112 for stimulation of the heart, a crystal clock 110, a random-access memory and read-only memory (RAM/ROM) unit 106 and a central processing unit (CPU) 104, all of which are well known in the art and described, for example, in U.S. Pat. No. 5,052,388 to Sivula et al, entitled "Method and Apparatus for Implementing Activity Sensing in a Pulse Generator." The Sivula et al. '388 patent is hereby incorporated by reference herein in its entirety. Cardiac leads 18 may consist of any typical lead configuration as is known in the art, such as, without limitation, right ventricular (RV) pacing leads, right atrial (RA) pacing leads, single pass RA/RV pacing leads, coronary sinus (CS) pacing leads, left ventricular pacing leads, epicardial leads, unipolar or bipolar lead configurations, or any combinations of the above lead systems. It is to be understood that the various components of IMD 20 depicted in FIG. 4 are powered by means of a battery (not shown), which is contained within the hermetic enclosure of IMD 20, in accordance with common practice in the art. The battery can comprise one or two conventional LiCF$_x$, LiMnO$_2$ or LiI$_2$ cells. For the sake of clarity in the figures, the battery and the connections between it and the other components of IMD 20 are not shown.

Upon detection of a cardiac anomaly, CPU 104, under control of firmware resident in RAM/ROM 106, will transmit event detection and high voltage capacitor charge start command to SubQ ICD 14 via communication link 26, will initiate recording of the appropriate diagnostic information into RAM of RAM/ROM 106, initiate a warning or alert to the patient, patient caregiver, or remote monitoring location and, upon reception of a charge complete confirmation from the SubQ ICD 14, initiate a shock command either asynchronously or, alternatively, synchronized to a sensed R-wave. A patient receiving the SubQ ICD 14 on a prophylactic basis would be instructed to report each such episode to the attending physician for further evaluation of the patient's condition and assessment of the need for implantation of a more sophisticated and long-lived ICD. (See logic flow diagram and illustration of FIG. 8, described hereinbelow).

Figure 4B:
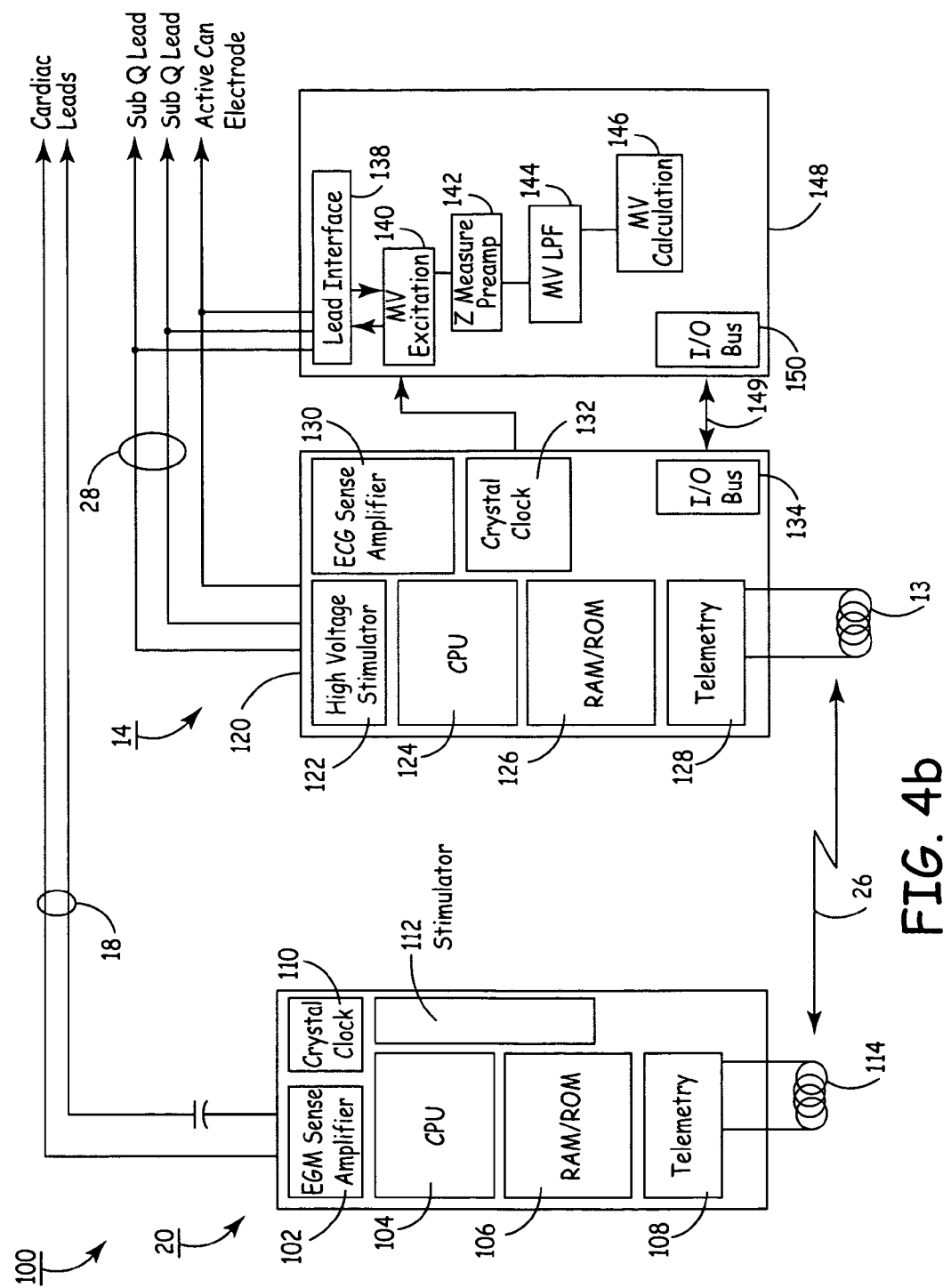
FIG. 4B illustrates an alternate embodiment of the circuitry of the SubQ ICD and IMD.

FIG. 4B illustrates the electronic circuitry that makes up the SubQ ICD 14 and IMD 20 of FIGS. 1-2 in accordance with the alternatively disclosed embodiment of the invention. To the extent that certain components of SubQ ICD 14 and IMD 20 are identical to that of the apparatus of FIG. 4A, they are labeled with the like number and perform the identical function. As illustrated in FIG. 4b, SubQ ICD 14 comprises a primary control circuit 120 and a minute ventilation MV circuit 148.

Primary control circuit 120 is coupled to minute ventilation circuit 148 by means of multiple signal lines, designated collectively as 149. An I/O interface 134 in primary control circuit 120 and a corresponding I/O interface 1550 in minute ventilation circuit 148, coordinate the transmission of signals between the two units via control lines 149.

Minute ventilation circuit 148 measures changes in transthoracic impedance, which has been shown to be proportional to minute ventilation. Minute ventilation is the product of tidal volume and respiration rate, and as such is a physiologic indicator of changes in metabolic demand and/or cardiac arrhythmias.

SubQ ICD 14, in accordance with the present invention, measures transthoracic impedance using subcutaneous lead (s) 28 and an electrode on the housing 14. As will be described hereinbelow in greater detail, minute ventilation circuit 148 delivers 30-microSec biphasic current excitation pulses of 1-mA (peak-to-peak) between a distal electrode of lead 18 and the conductive canister of SubQ ICD 14, functioning as an indifferent electrode CASE, at a rate of 16-Hz. The resulting voltage is then measured between the electrode of lead 28 and the SubQ ICD 14 active can electrode.

The impedance signal derived by minute ventilation circuit 148 has three main components: a DC offset voltage; a cardiac component resulting from the heart's function; and a respiratory component. The frequencies of the cardiac and respiratory components are assumed to be identical to their physiologic origin. Since the respiratory component of the impedance signal derived by minute ventilation circuit 148 is of primary interest for this aspect of the present invention, the impedance signal is subjected to filtering in minute ventilation low-pass filter (MV LPF) 144 having a passband of 0.05- to 0.8-Hz (corresponding to 3-48 breaths per minute) to remove the DC and cardiac components.

With continuing reference to FIG. 4B, minute ventilation circuit 148 includes a Lead Interface circuit 138 which is essentially a multiplexer that functions to selectively couple and decouple minute ventilation circuit 148 to the subcutaneous lead(s) 28 and active can electrodes, as will be hereinafter described in greater detail.

Coupled to lead interface circuit 138 is a minute ventilation (MV) Excitation circuit 140 which functions to deliver the biphasic constant-current pulses between various combinations of lead electrodes (subcutaneous lead(s), active can, etc.) for the purpose of measuring thoracic impedance. In particular, MV Excitation circuit 140 delivers biphasic excitation pulses (at a rate of 16-Hz between the distal subcutaneous electrode and the canister 14 active can electrode) of the type delivered in accordance with the method and apparatus described in U.S. Pat. No. 5,271,395 "Method and Apparatus for Rate Responsive Cardiac Pacing" to Wahlstrand et al., which is commonly assigned to the assignee of the present invention and hereby incorporated by reference herein in its entirety.

With continued reference to FIG. 4b, the 16-Hz sampled output voltages from Z Measure Preamp circuit 142 are presented to the minute ventilation low-pass filter circuit MV LPF 144, which has a passband of 0.05-0.8 Hz in the presently preferred embodiment of the invention. Again, it is believed that the design and implementation of MV LPF circuit 144 would be a matter of routine engineering to those of ordinary skill in the art. The output from MV LPF circuit 144 is a voltage waveform whose level at any given time is directly proportional to thoracic impedance measured between the selected electrodes. Thus, the MV LPF output signal will be referred to herein as an impedance waveform. MV Calculation 140 analyzes the impedance waveform to determine/detect respiration rate, tidal volume, minute ventilation and presence of apnea.

The circuit of FIG. 4B may optionally monitor pulmonary edema for congestive heart failure patients (CHF) by measuring the DC impedance between the distal electrodes of subcutaneous lead(s) 28 and the housing of SubQ ICD 14. The measurement technique may be as substantially described in U.S. Pat. No. 6,512,949 "Implantable Medical Device for Measuring Time Varying Physiologic Conditions Especially Edema and for Responding Thereto" by Combs, et al incorporated herein by reference in its entirety.

Upon detection of a cardiac arrhythmia from monitoring the ECG signal and/or detection of a respiration anomaly, CPU 124, under control of firmware resident in RAM/ROM 126, will initiate recording of the appropriate diagnostic information into RAM of RAM/ROM 126, and initiate a transmission to IMD 20 via communication channel 26. Subsequent therapy commands will be sent to SubQ ICD 14 from IMD 20.

CPU 104, in conjunction with software program in RAM/ROM 106, integrates the information from the sensed cardiac EGM signals, sensed ECG signals and any sensor signals/data, detects the onset of cardiac anomalies, provides preprogrammed cardiac stimulation via cardiac lead(s) 18, communicates arrhythmia therapy commands to SubQ ICD 14 via communication link 26 and, formats and stores diagnostic data for later retrieval by the patient's clinician and, optionally, may warn or alert the patient, patient caregiver or remote monitoring location. A patient receiving the SubQ ICD 14 on a prophylactic basis would be instructed to report each such episode to the attending physician for further evaluation of the patient's condition and assessment for the need for implantation of a more sophisticated and long-lived ICD. See flow diagram and description as described below in association with FIG. 8.

Optionally, IMD 20 of FIG. 4B may include alternative sensors to aid in the detection and confirmation of arrhythmias. Hemodynamic sensors such as perfusion (i.e., $O_2$sat, see U.S. Pat. No. 4,791,935 "Oxygen Sensing Pacemaker" to Baudino et al), pressure (as described in U.S. Pat. No. 5,368,040 "Apparatus and Method for Determining a Plurality of Hemodynamic Variables from a Single, Chronically Implanted Absolute Pressure Sensor" to Carney and U.S. Pat. No. 4,485,813 "Implantable Dynamic Pressure Transducer System" to Anderson, et al), mechanical (accelerometer), and heart sounds (as described in U.S. Pat. No. 5,554,177 "Method and Apparatus to Optimize Pacing Based on Intensity of Acoustic Signal" to Keival) and respiration (as described in U.S. Pat. No. 5,271,395 "Method and Apparatus for Rate-Responsive Cardiac Pacing" to Wahlstrand). The Baudino '935, Carney '040, Anderson '813, Keival '177 and Wahlstrand '395 patents are incorporated herein by reference in their entireties. The epicardial pacemaker of FIG. 2 may also optionally include epicardial based sensors such as a stretch (i.e., strain gauge) sensor, mechanical motion (i.e., accelerometer) and pressure sensor.

Figure 5:
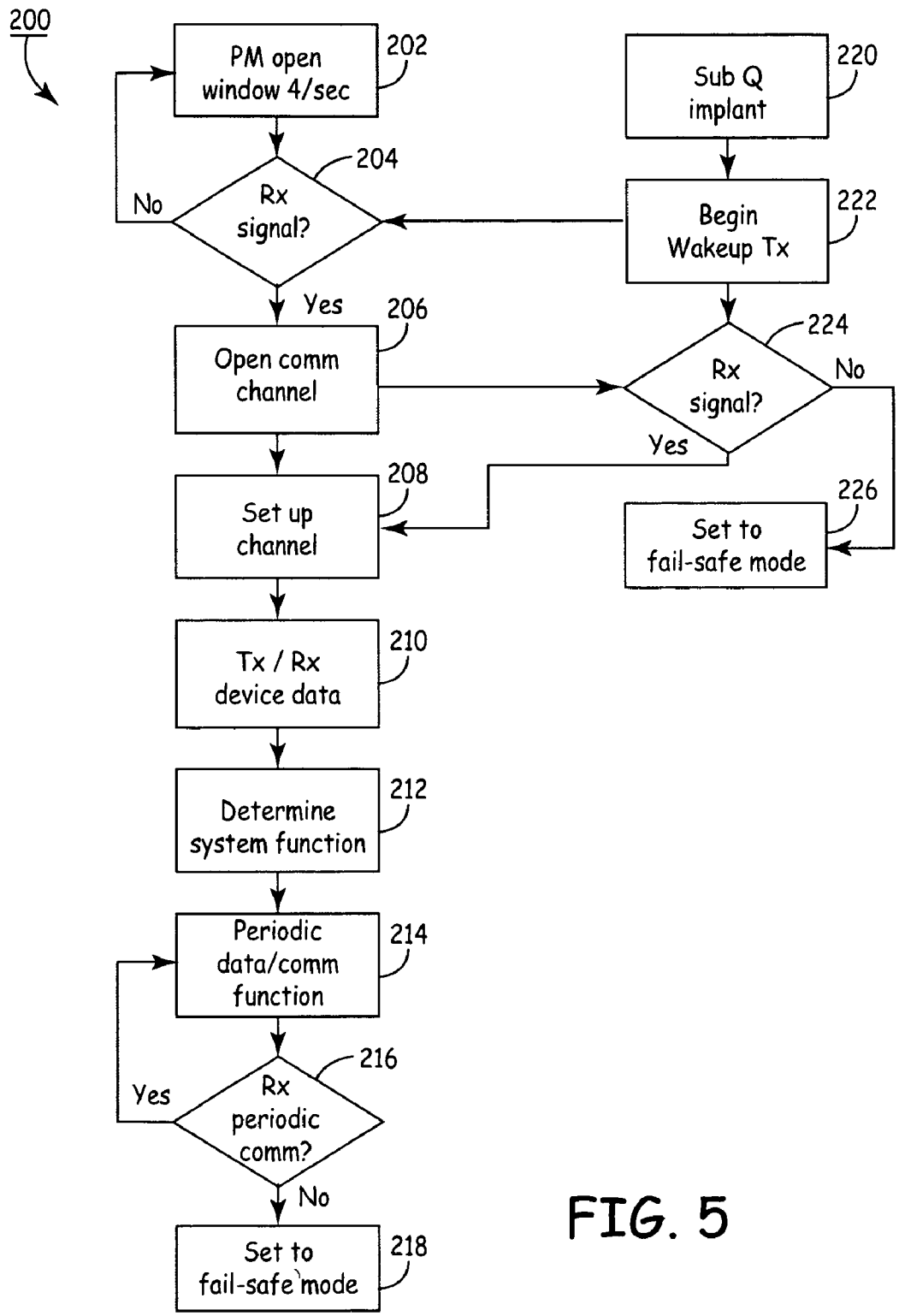
FIG. 5 illustrates a logic flow diagram relating to the method of initialization of the bi-directional communication channel of the SubQ ICD and IMD.

FIG. 5 is a logic flow diagram illustrating the desired method of initialization of the low power bi-directional communication channel of the SubQ ICD 14 and IMD 20 (FIG. 1) or 30 (FIG. 2) upon implant. Note that the use of periodic window receiver operation reduces the average current drain from the battery by up to $\frac{1}{1000}$. In a previously implanted pacemaker, at step 202 a receiver window (10 uSec to 1 mSec, typically 100 uSec) is opened 1 to 8 (preferably 4) times per second allowing a receiver telemetry circuit to detect an RF signal if present. If a RF signal is received at step 204, the flow diagram opens a bi-direction communication channel at step 206. If at step 204 the proper RF signal is not sensed in the window, the flow diagram returns to step 202 to wait till a timer in the IMD 20 triggers the next window opening.

Upon the implant of a SubQ ICD 14, at step 220 the SubQ ICD detects the successful implant via an impedance test between the distal electrode on subcutaneous lead 28 and the electrode on SubQ ICD 14. Alternatively, an external programmer may initiate the bi-directional channel setup via a downlink telemetry command. At step 222 the SubQ ICD begins wakeup transmission communication to any implantable medical device located in patient 12. At step 224, the SubQ ICD looks for a response from an implanted medical device. If it receives the proper response to its wakeup transmission at step 224, it begins bi-direction communication with the implanted device to set up the communication channel. The channel setup may include information from each device to synchronize internal clocks, setup predetermined bit error rates (BER), setup transmission speed between devices (which may be different in each direction), setup transmission power between devices (which may be different in each direction), setup communication window details, i.e., window width, window timing and window duty cycle, i.e., times per second. If at step 224 the SubQ ICD does not receive an answer to its wakeup transmission, at step 226 it sets its function to a fail-safe mode as a standalone defibrillator.

At step 210 the 2 devices, SubQ ICD 14 and IMD 20, or alternatively epicardial device 30, begin a transmission and reception of device data such as hardware, software, firmware, battery and sensor capabilities and status and any diagnostic data that may be appropriate (such as under/over sensing, sensor problems, etc.). At step 212 the 2 devices, SubQ ICD 14 and IMD 20, or alternatively 30, determine system function (i.e., master/slave relationship, sensors available, verify detection and therapy details, etc.).

At step 214 the 2 devices, SubQ ICD 14 and IMD 20, or alternatively epicardial device 30, begin periodic data and event communication providing current updates on device status (such as hardware, software, firmware, battery and sensor status), clock resynchronization data and any diagnostic/event data (such as sensed/paced events, sensor events/values, arrhythmia detection, high voltage charge start, high voltage stimulation (i.e., pace stimulus) or shock.

At step 216 the flow diagram tests for the reception of the periodic communication from the other implanted device. If reception is confirmed, it continues the periodic data communication function at step 214. If at step 216 either device fails to receive the periodic transmission, each device switches to a predetermined fail-safe mode (i.e., as a standalone device, as a pacemaker and/or SubQ ICD.

Figure 6:
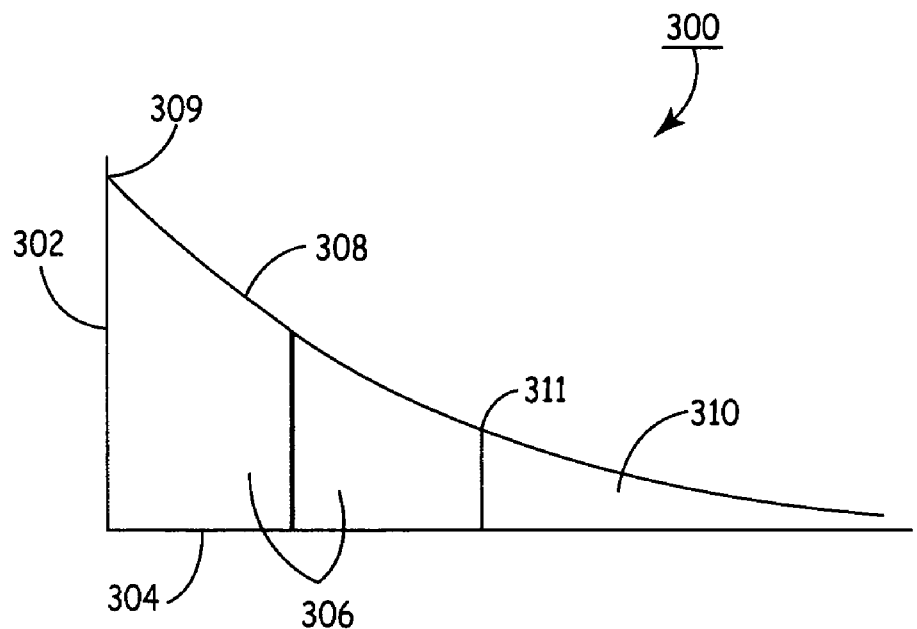
FIG. 6 illustrates the voltage on the high voltage output capacitors of the SubQ ICD.

FIG. 6 illustrates voltage 302, on the high voltage output capacitors, versus time 304 of the SubQ ICD of FIG. 4. Upon detection of an arrhythmia, the high voltage capacitors are charged typically to 750 volts (309 in FIG. 6). The first phase of the high voltage cardioversion or defibrillation biphasic pulse 306 drops the capacitor voltage typically to 65% (309 in FIG. 6) while the second phase drops the capacitor voltage to 40% (311 in FIG. 6). At this time, the SubQ ICD 14 optionally may begin high voltage pacing (typically programmable from 0.5 to 1.5 mSec pulse width) to support the heart rate post shock with the voltage remaining on the high voltage capacitors.

Figure 7:
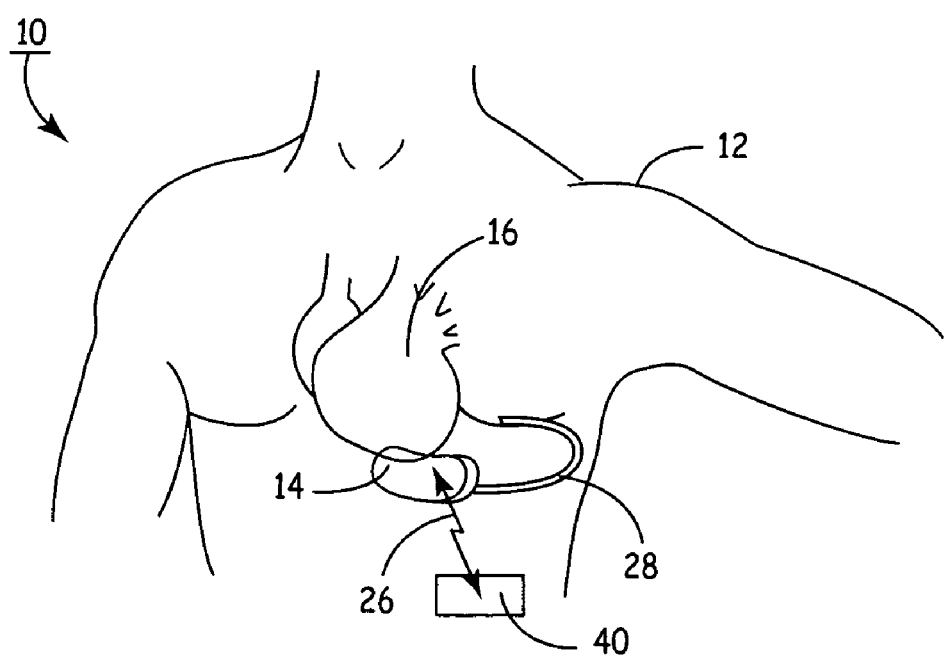
FIG. 7 illustrates the SubQ ICD and a drug delivery device implanted in a patient.

FIG. 7 illustrates SubQ ICD 14 and a transdermal drug delivery apparatus 40 of an alternative embodiment of the present invention. The drug delivery device 40, in communication with at least one IMD, is externally mounted to deliver pain analgesics and/or threshold reduction medicants prior to or contemporaneous with a stimulus or shock associated with the SubQ ICD 14. The drug delivery device includes an attachable strip with storage for medicants and is epidermally mounted on the patient's arm or torso. The medicants are released into the bloodstream in response to an indication that the SubQ ICD 14 has detected an arrhythmia and is about to deliver a shock and/or beginning to deliver high voltage pacing stimulus. The drug delivery device 40 is adapted for use with various pain reducing drugs such as opiates (i.e., morphine sulfate and hydromorphine) or non-opiates (i.e., alpha-2 adreneorgic agonists and neuron specific calcium channel blocking agents). Alternatively, the drug delivery device 40 may deliver defibrillation threshold reducing agents such as D-salotol, Procainamade or Quinidine as alternatives or in combination with one or both said opiates and non-opiates. Further, the delivery of drugs could be initiated by the patient to provide a semi-automatic use by using a patient activator or, alternatively, pushing a button on the transdermal drug delivery device 40. Because it may take 30 seconds or more for the drugs to begin taking effect and the arrhythmia may be life threatening, the SubQ ICD 14 does not wait for the drugs to take effect before delivering the shock therapy or high-voltage pacing stimulus. Rather the pain medication is desirably intended for post shock pain relief.

Alternatively, the system of FIG. 7 as described above may additionally include IMD 20 as shown in FIGS. 1 and 2. And optionally further, the transdermal drug delivery apparatus 40 may be controlled by IMD 20 singularly or alternatively, in combination with SubQ ICD 14.

Figure 8:
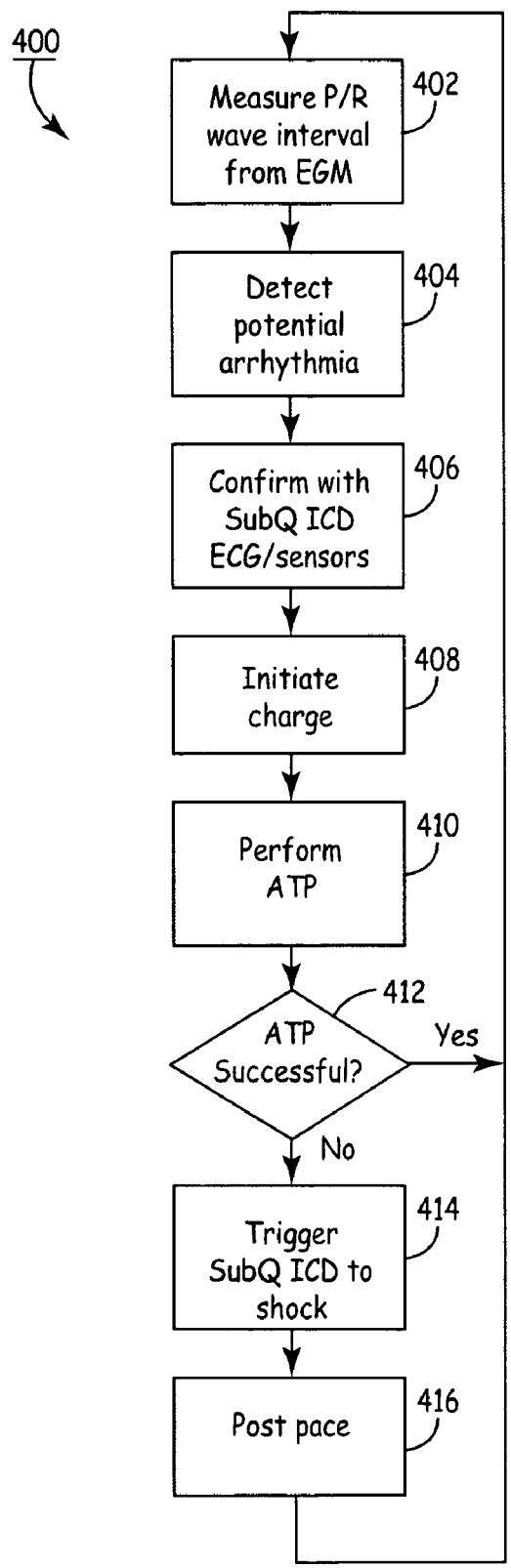
FIG. 8 illustrates a logic flow diagram relating to detections and therapy delivery by the SubQ ICD and IMD.

FIG. 8 illustrates a logic flow diagram relating to a method of detection and therapy delivery of the system depicted in FIGS. 1 and 2 including a SubQ ICD 14 and IMD 20. IMD 20 measures the P-P, R-R and P-R intervals of signals from the EGM sense amplifier 102 at step 402. At step 404 the IMD detects a potential arrhythmia. At step 406 IMD 20 confirms the arrhythmia with sensed data from SubQ ICD 14 via communication channel 26 and/or with signals from sensors such as described above with respect to FIG. 4b. This reconfirmation of an arrhythmia may include comparing sensed events from each signal (i.e., EGM from IMD 20 and ECG from SubQ ICD sense amplifiers and detection algorithms). Alternatively, this reconfirmation may consist of cross checking the arrhythmia detection from signals from sensors as described above with respect to FIG. 4b. The patient's physician may program a weighting ratio to modify the relative impacts of sensor signals/events versus sensed cardiac signals. At step 408, IMD 20 sends a signal to SubQ ICD 14 via communication channel 26 to begin high voltage charging of the high voltage capacitors. At step 410, IMD performs antitachy pacing (i.e., ATP). At step 412, IMD monitors the EGM signals from intracardiac leads 18 to determine whether the arrhythmia was successfully terminated. If the ATP stimulation is successful, the logic returns to measuring/monitoring P/R waves at step 402. If at step 412, ATP pacing is found to not be successful, IMD 20 sends a shock trigger signal to SubQ ICD 14 via communication channel 26 at step 414. This signal may be an asynchronous trigger for defibrillation or, alternatively, a synchronizing trigger based upon a sensed R-wave to provide for a cardioversion stimulus. After the shock is delivered by SubQ ICD 14, IMD 20 provides post shock pacing support at step 416. Upon completion of post shock support pacing, the flow diagram 400 returns to measuring/monitoring P/R waves at step 402.

In the logic flow diagram of FIG. 8 at step 406, alternatively the endocardial or epicardial R-waves from the cardiac leads 18 sensed by the amplifier 102 in IMD 20 may be compared directly with the EGM sensed far-field R-waves sensed by SubQ ICD 14 ECG sense amplifier by time shifting one or the other, or both, to verify proper detection. One method to allow an accurate time shift is to periodically provide a refractory paced event to allow proper near and far field signal alignments.

Also optionally at step 406 an $O_2$sat or pressure hemodynamic sensor located in each IMD 20 and SubQ ICD 14 allows for systemic gradients to allow improved specificity, confirmation of sensing and diagnosis of arrhythmia and/or the optimization of IMD/SubQ ICD parameters such as A-V delay, rate and mode.

Figure 9:
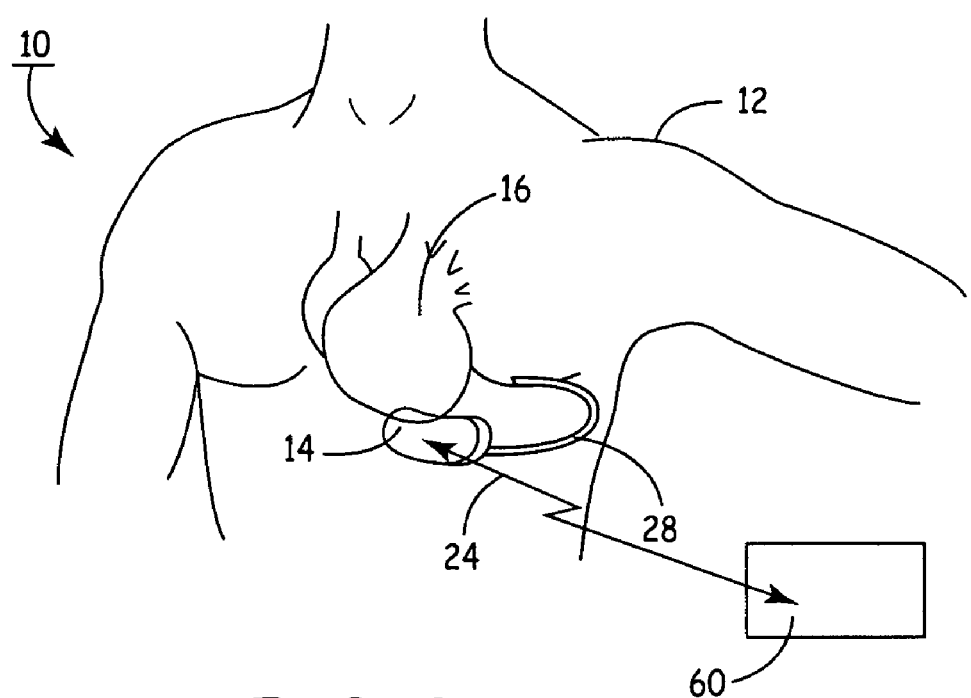
FIG. 9 illustrates the SubQ ICD implanted in a patient and being in data communication with an AED.

FIG. 9 illustrates SubQ ICD 14 and lead 28 implanted in patient 12 as described above in relation to FIG. 3. FIG. 9 additionally shows an automatic external defibrillator (AED) 60 in close proximity to patient 12 (defibrillation patches typically connected to the patient's torso are not shown in FIG. 9 for clarity). The AED 60 upon being switched on and being in close proximity to the SubQ ICD 14, may begin to set up a communication channel as described above connects with FIG. 5. The AED 60 may then utilize the sensed events and/or optional sensor data from the SubQ ICD 14 to aid in arrhythmia detection/confirmation and/or shock synchronization. The two devices, SubQ ICD 14 and AED 60 may synergistically shock simultaneously to sum their fields, or optionally, shock with a slight delay to provide slightly different vectors. Optionally, the AED may communicate a warning to the SubQ ICD 14 to allow the implanted device to take protective measures prior to and during an external shock.

Alternatively, the system of FIG. 9 as described above may additionally include the IMD 20 as shown in FIGS. 1 and 2. And optionally further, the AED 60 may be controlled by IMD 20 singularly or alternatively, in combination with SubQ ICD 14.

Alternatively, the system of the present invention may provide synergistic communication and function between a SubQ ICD 14 and/or an IMD 20 and an externally worn temporary defibrillator commonly configured as a vest as substantially described in U.S. Pat. No. 6,280,461 "Patient-worn Energy Delivery Apparatus" to Glegyak, et al and incorporated herein by reference in its entirety. The temporary defibrillator/vest, upon being switched on and being in close proximity to the SubQ ICD 14 and/or IMD 20, may begin to set up a communication channel as described hereinabove. The defibrillator/vest may then utilize the sensed events and/or optional sensor data from the SubQ ICD 14 and/or IMD 20 to aid in arrhythmia detection/confirmation and/or shock synchronization. The two devices, SubQ ICD 14 and defibrillator/vest may synergistically shock simultaneously to sum their fields, or optionally, shock with a slight delay to provide slightly different vectors. Optionally, the defibrillator/vest may communicate a warning to the SubQ ICD 14 and/or IMD 20 to allow the implanted device to take protective measures prior to and during an external shock.

Optionally the systems as described above in connection with FIGS. 1-9 may include coordinated programming and telemetry/diagnostics screen displays and similar programming controls. This will allow a safe, effective and clear programming and the proper monitoring of the patient's condition as well as the status/function of the devices. For example, instead of having to program stimulation rates, modes, sensitivity settings, arrhythmia detection zones, various therapy details (i.e., cardioversion shock, ATP details, defibrillation shock, etc.) in multiple devices, one programmer screen display may be used where these details are selected once and then used to program the multiple devices without further efforts by subsequent users.

It will be apparent from the foregoing that while particular embodiments of the invention have been illustrated and described, various modifications can be made without departing from the spirit and scope of the invention. Accordingly, it is not intended that the invention be limited, except as by the appended claims.

The invention claimed is:

1. A system for automatic arrhythmia therapy delivery to a patient, comprising:
a subcutaneous, implantable cardioverter-defibrillator (SubQ ICD) device adapted to be implanted outside the thoracic cavity, the SubQ ICD being capable of detecting cardiac events indicative of an arrhythmia and delivering a shock therapy;
an implantable pulse generator (IPG) device having leads adapted for connection to a patient's heart, the IPG device being capable of detecting cardiac events indicative of an arrhythmia and delivering a pacing therapy;
means for establishing bi-directional communication between the Sub Q ICD device and the IPG device configured to transmit data upon detection by either device of a cardiac event indicative of an arrhythmia;
means for obtaining a confirmation of an existence of cardiac events indicative of an arrhythmia by comparing a cardiac event indication of the SubQ ICD with a cardiac event indication of the IPG device; and
means for commanding delivery of a therapy upon detection of a cardiac event indicative of an arrhythmia based on the data transmitted via the bi-directional communication and a specific capability of each of the SubQ ICD device and the IPG device, wherein, in response to detection of a cardiac event indicative of an arrhythmia and obtaining the confirmation, the IPG is commanded to deliver a pacing therapy and in response to continued detection of a cardiac event indicative of an arrhythmia the SubQ ICD is commanded to deliver a shock therapy.

2. The system of claim 1 wherein said means for enabling bi-directional communication includes an RF signal.

3. The system of claim 1 wherein the IPG device transmits a signal to the SubQ ICD device to begin charging a high voltage capacitor upon detection of a cardiac event indicative of an arrhythmia and delivers a pacing therapy to terminate a presence of a cardiac event indicative of an arrhythmia.

4. The system of claim 1 wherein the IPG device provides post-shock support pacing.

5. The system of claim 1 wherein said IPG device includes a hemodynamic sensor to sense at least one of perfusion ($O_2$ saturation), pressure, and respiration.

6. The system of claim 5 wherein said hemodynamic sensor includes at least one of nanoteeth/electrodes, a stretch sensor, a strain gauge and epicardial fixation.

7. The system of claim 1 wherein each of said SubQ ICD device and said IPG device communicates with an automatic external defibrillator (AED) device and includes an algorithm for automatic connectivity.

8. The system of claim 1 wherein a remote data transfer device is implemented to uplink data to a remote programmer for processing data or a downlink to modify or update data in each one of the SubQ ICD device and the IPG device.

* * * * *